(12) United States Patent
Alexandersson

(10) Patent No.: US 10,127,836 B2
(45) Date of Patent: Nov. 13, 2018

(54) AUTOMATIC INJECTION TRAINING DEVICE

(71) Applicant: Carebay Europe Ltd, Swatar (MT)

(72) Inventor: Oscar Alexandersson, Haninge (SE)

(73) Assignee: Carebay Europe Ltd, Sliema (MT)

( * ) Notice: Subject to any disclaimer, the term of this patent is extended or adjusted under 35 U.S.C. 154(b) by 660 days.

(21) Appl. No.: 14/434,782

(22) PCT Filed: Oct. 8, 2013

(86) PCT No.: PCT/EP2013/070878
§ 371 (c)(1),
(2) Date: Apr. 10, 2015

(87) PCT Pub. No.: WO2014/056868
PCT Pub. Date: Apr. 17, 2014

(65) Prior Publication Data
US 2015/0235571 A1    Aug. 20, 2015

Related U.S. Application Data

(60) Provisional application No. 61/712,299, filed on Oct. 11, 2012.

(30) Foreign Application Priority Data

Oct. 11, 2012 (SE) ...................................... 1251149

(51) Int. Cl.
G09B 23/00    (2006.01)
G09B 23/28    (2006.01)
A61M 5/315   (2006.01)

(52) U.S. Cl.
CPC ....... *G09B 23/285* (2013.01); *A61M 5/31501* (2013.01)

(58) Field of Classification Search
None
See application file for complete search history.

(56) References Cited

U.S. PATENT DOCUMENTS

| 5,071,353 A | 12/1991 | van der Wal |
| 2007/0111175 A1 | 5/2007 | Raven et al. |
| 2012/0015336 A1 | 1/2012 | Mach |

FOREIGN PATENT DOCUMENTS

| WO | 2009/105908 A1 | 9/2009 |
| WO | 2011/151315 A1 | 12/2011 |

OTHER PUBLICATIONS

EPO, Int'l Search Report in PCT/EP2013/070878, dated Jan. 7, 2014.
EPO, Written Opinion in PCT/EP2013/070878, dated Jan. 7, 2014.

*Primary Examiner* — James Hull
(74) *Attorney, Agent, or Firm* — Piedmont Intellectual Property

(57) ABSTRACT

Automatic injection training device with a housing assembly comprising an outer housing, an actuation assembly, and a damper unit comprising a damper housing and a piston assembly that is arranged in said damper housing. The damper housing slides in a proximal direction relative to the piston assembly when an injection is simulated.

13 Claims, 13 Drawing Sheets

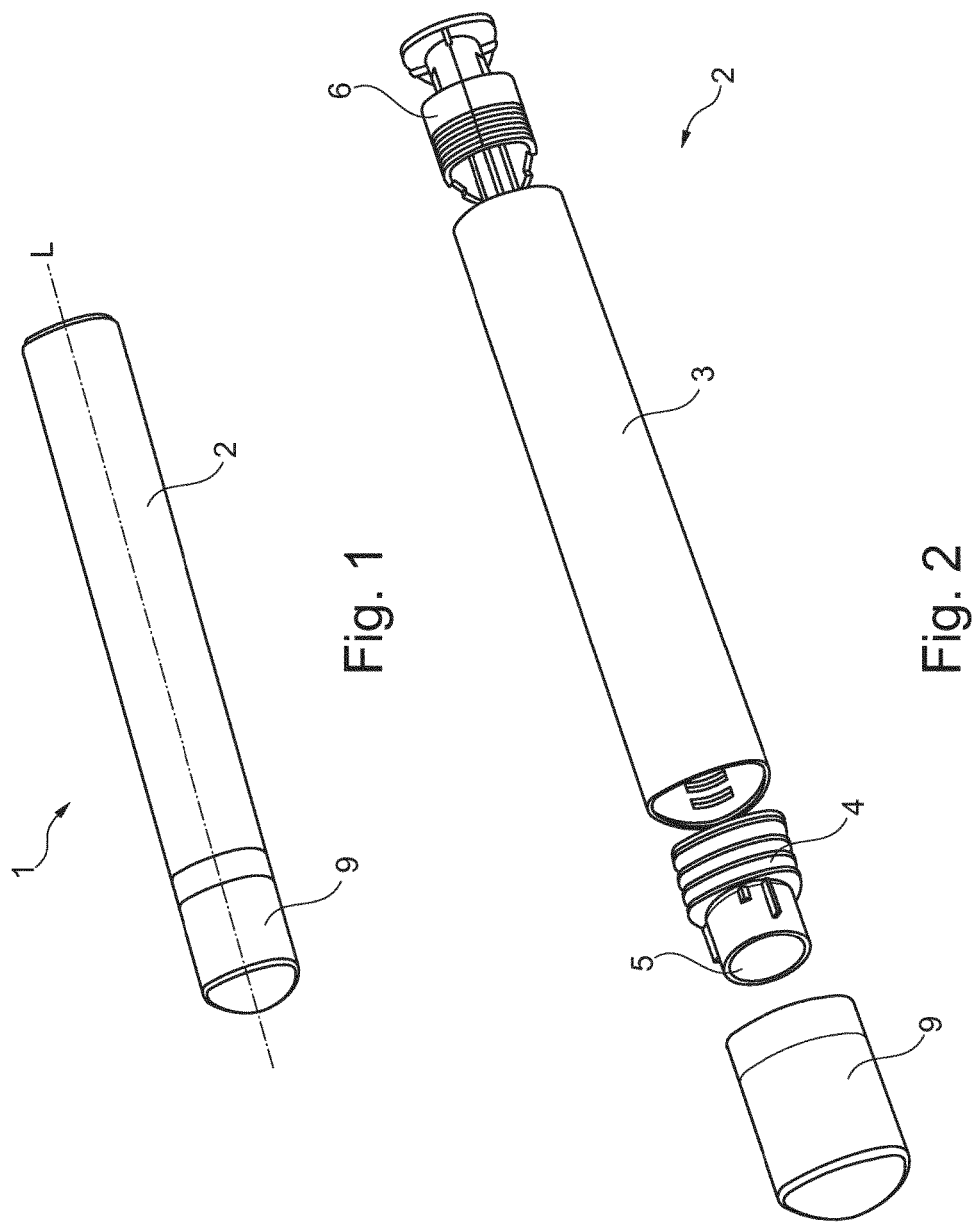

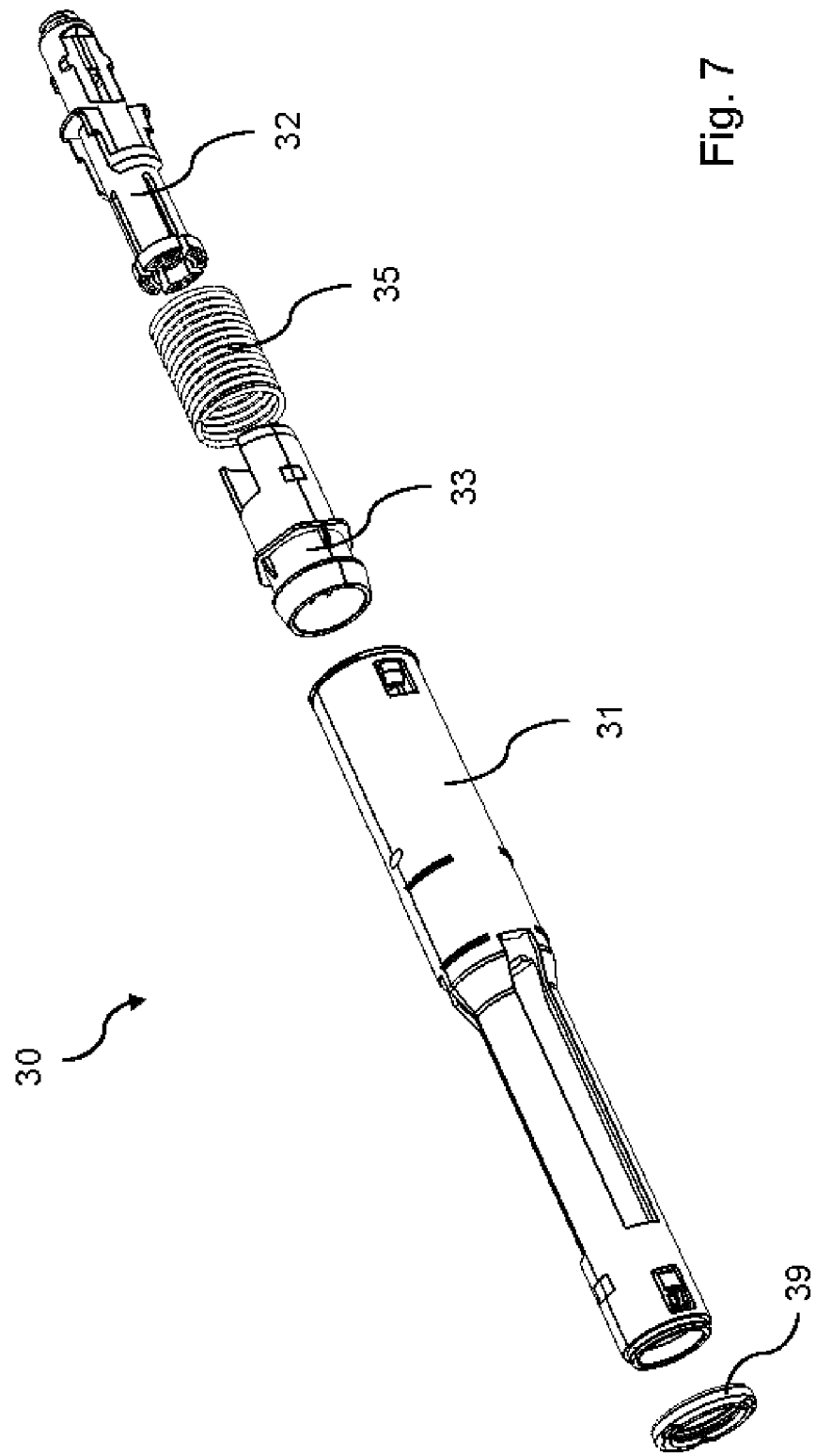

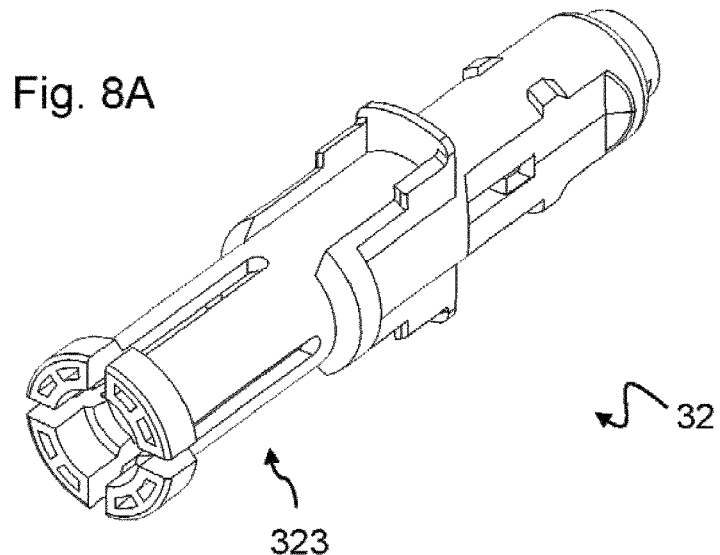
Fig. 8A
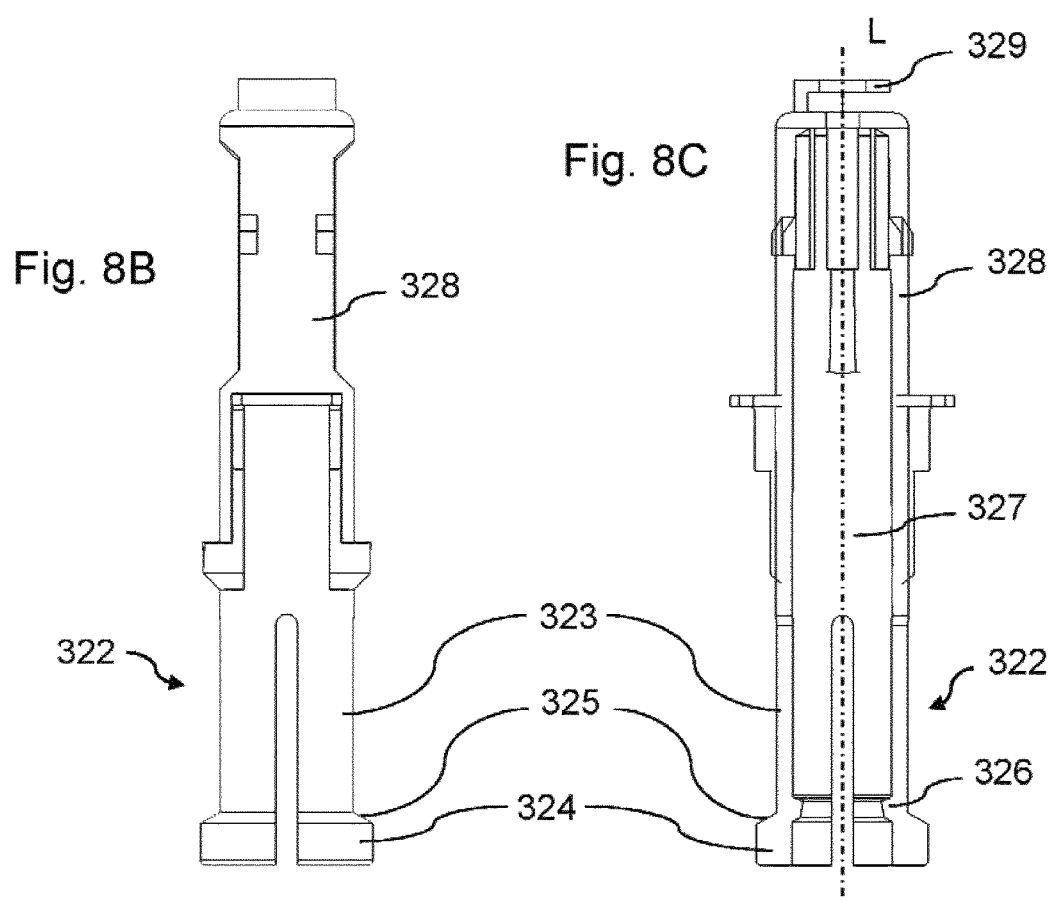

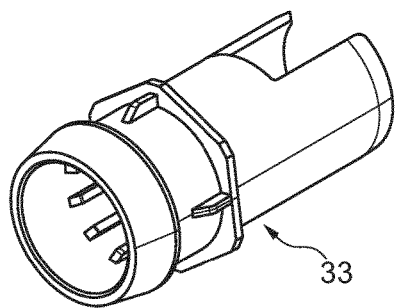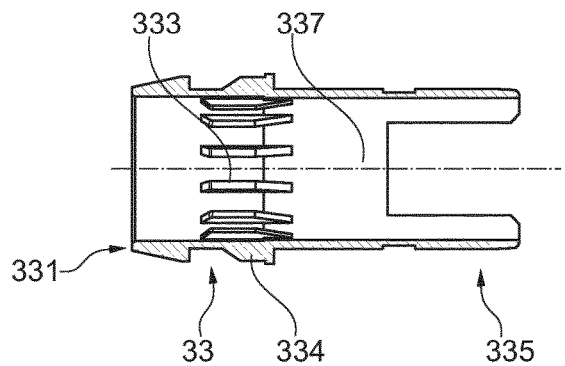
Fig. 9A          Fig. 9B
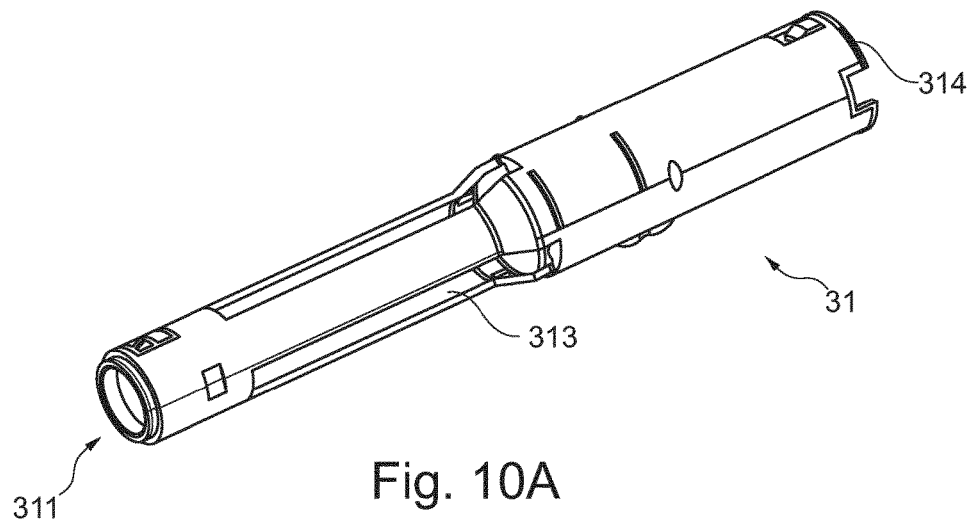
Fig. 10A
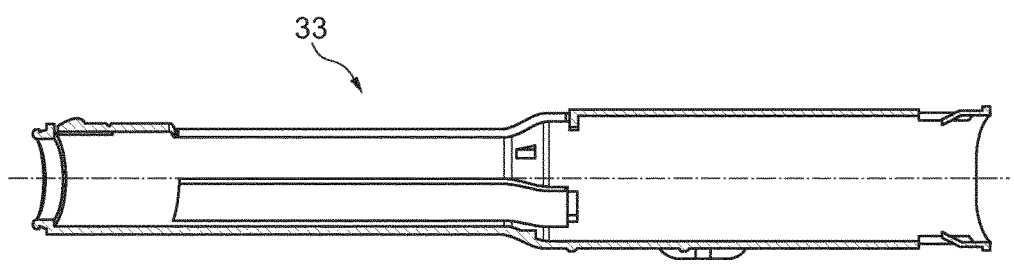
Fig. 10B

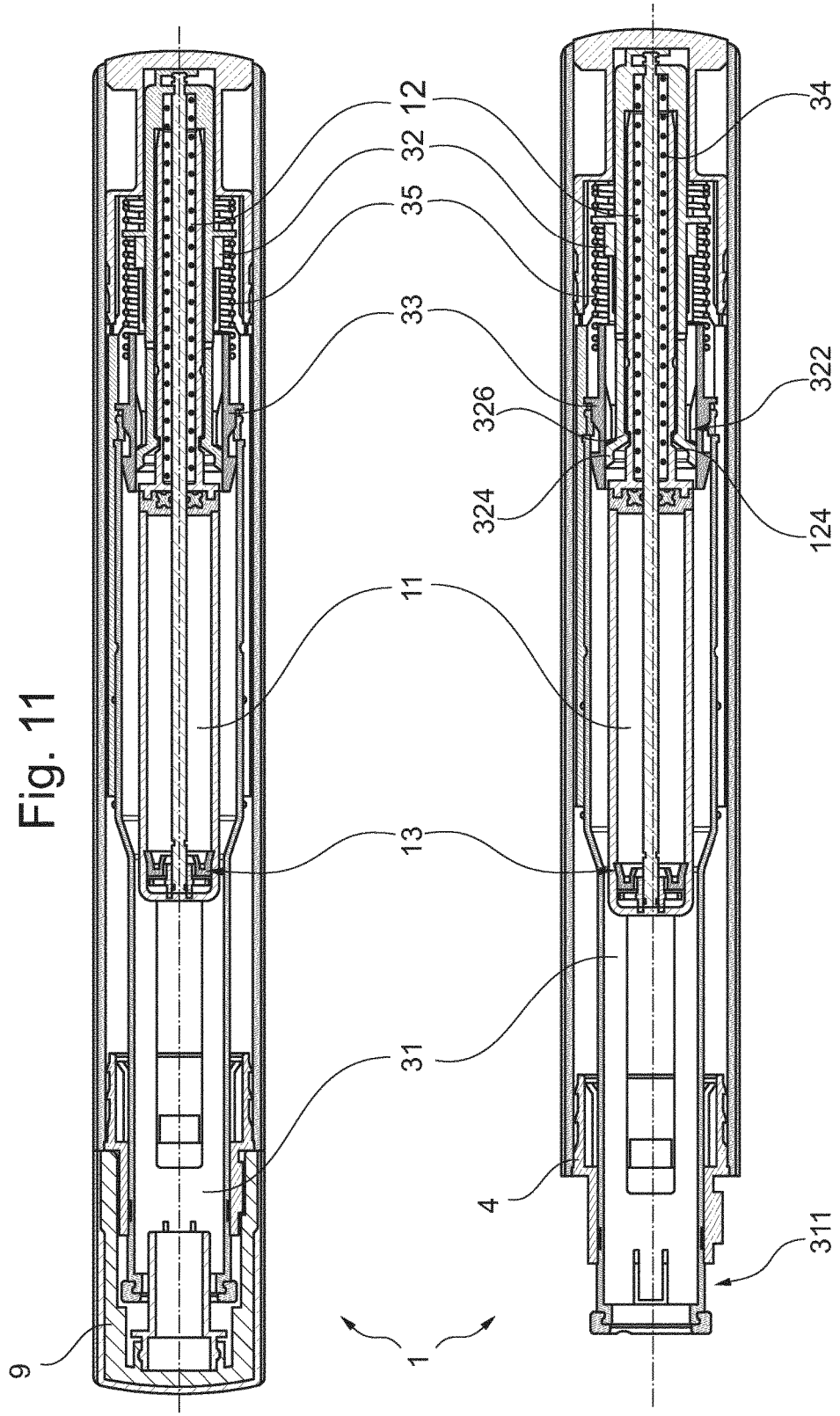

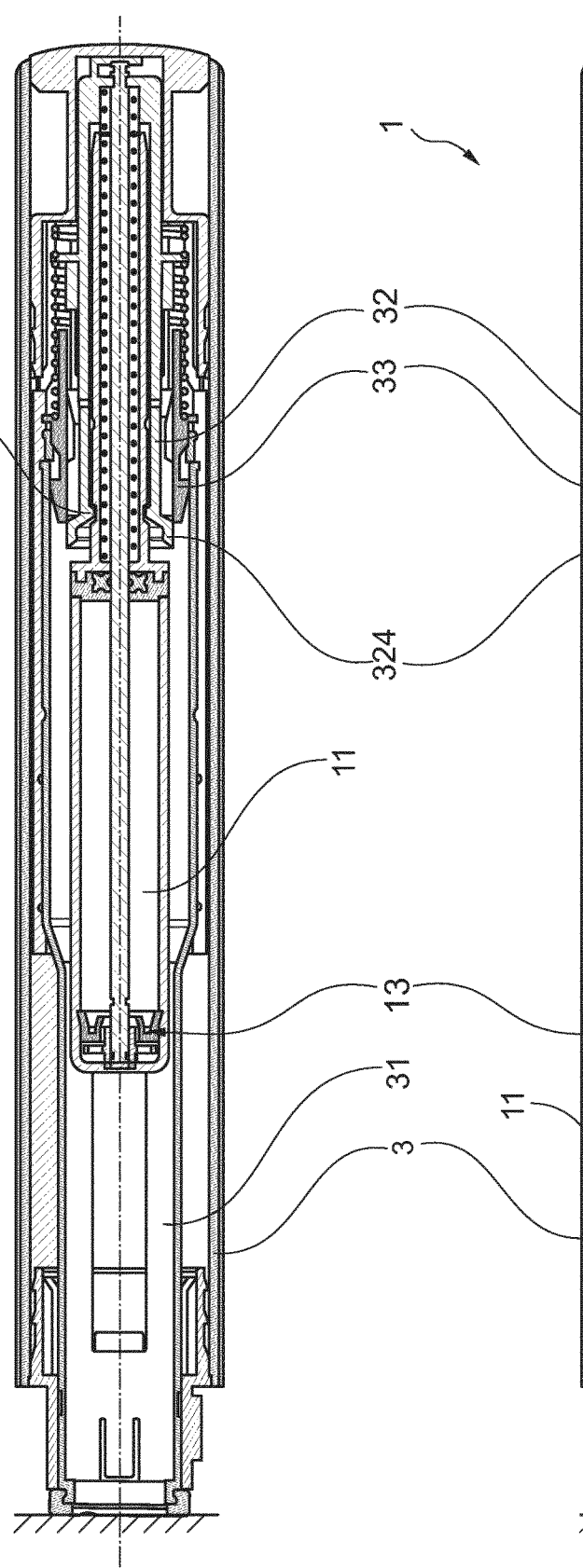
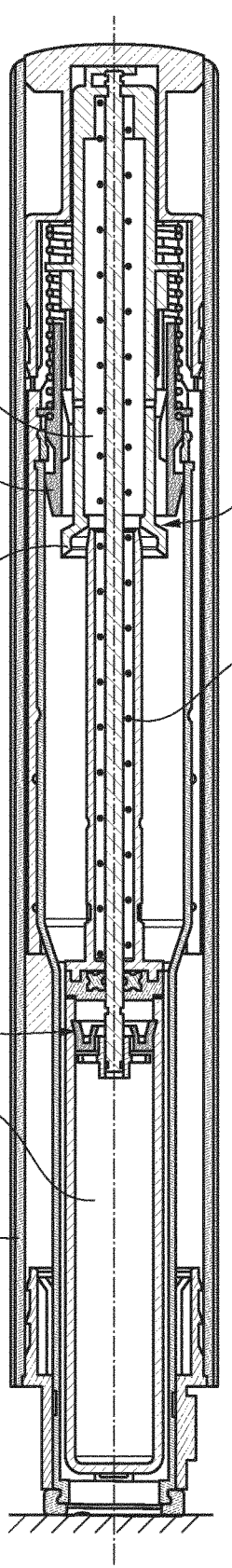

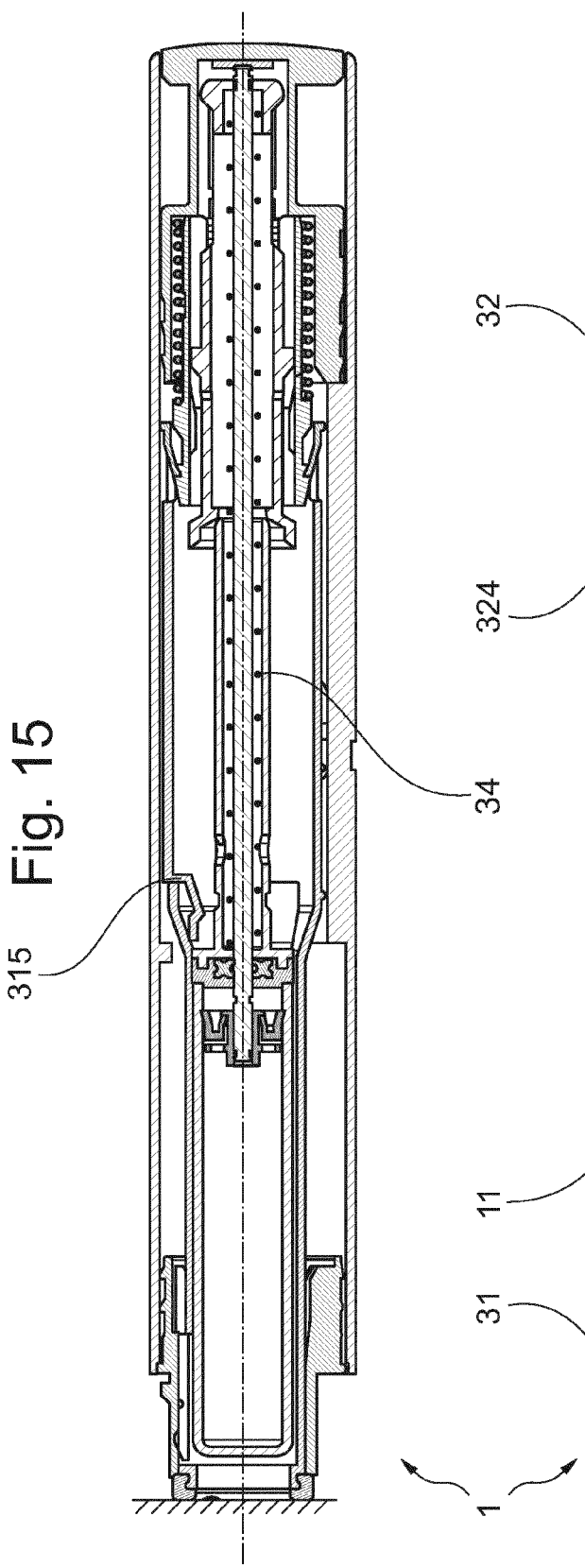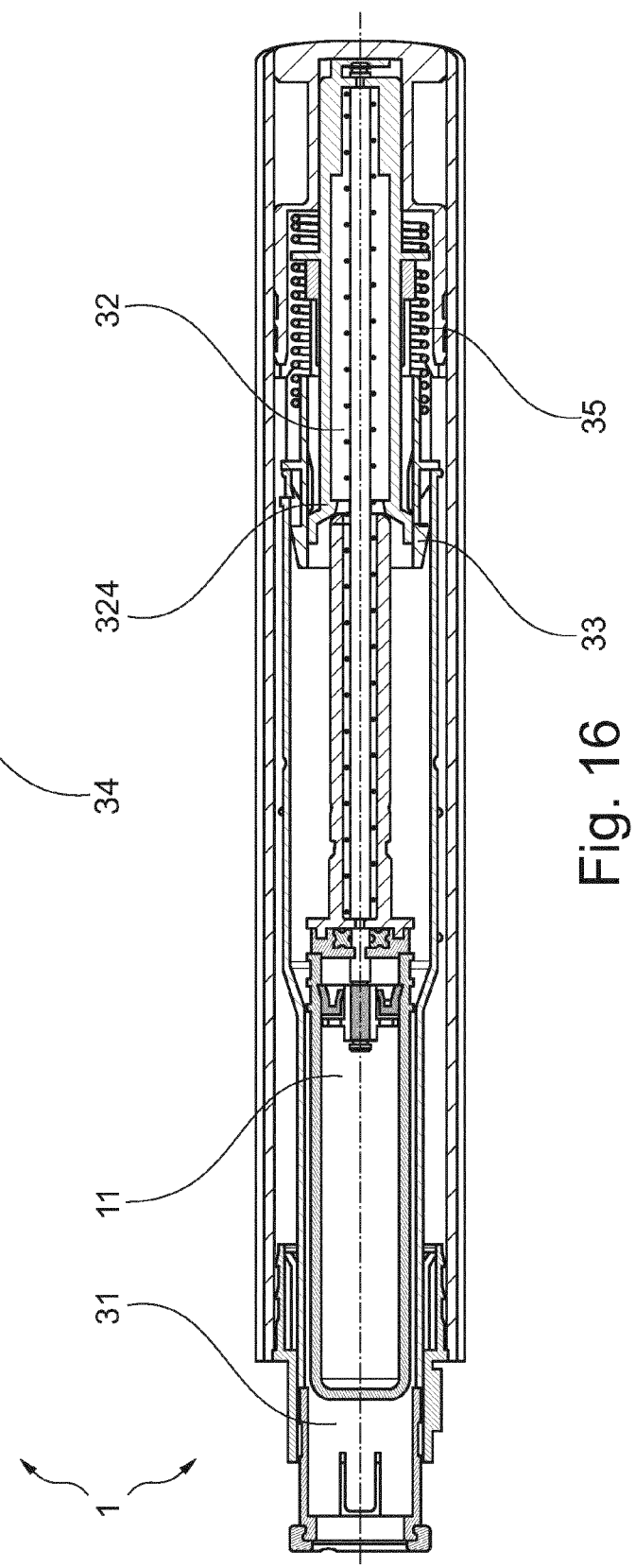

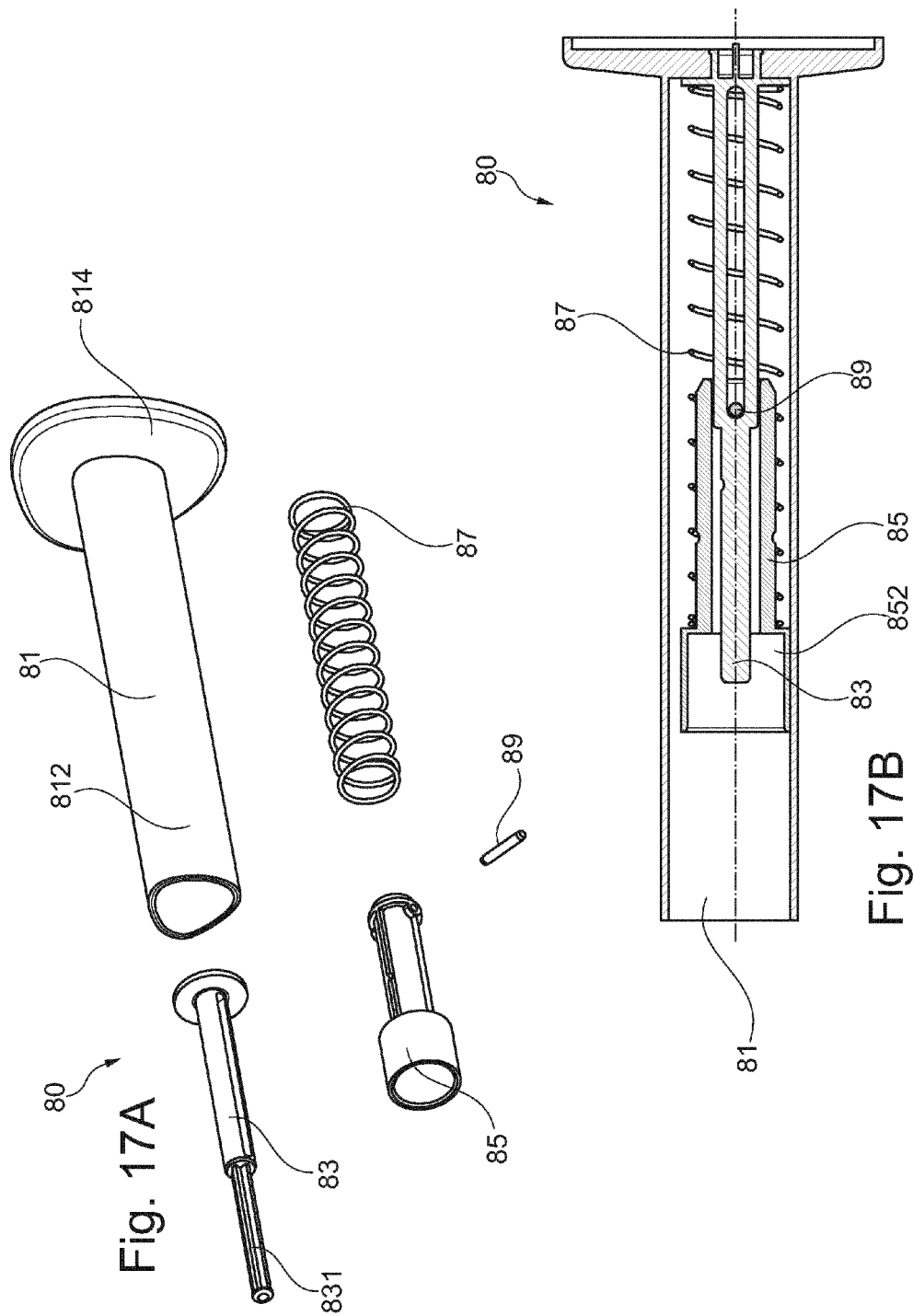

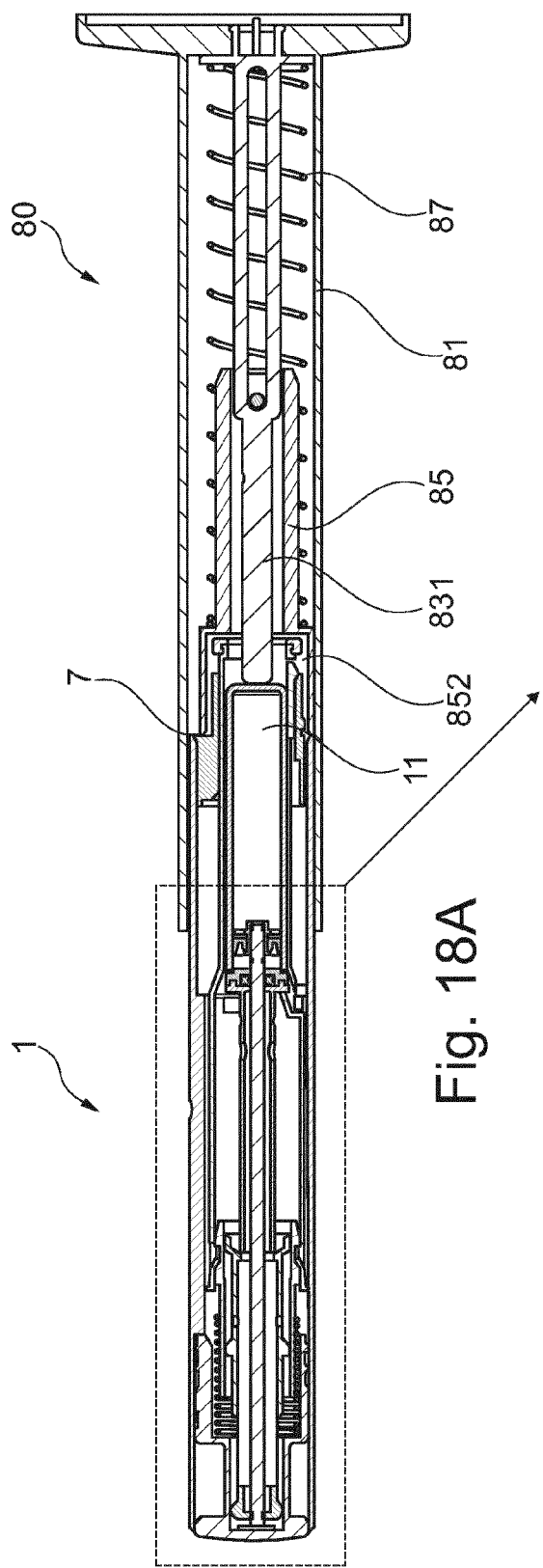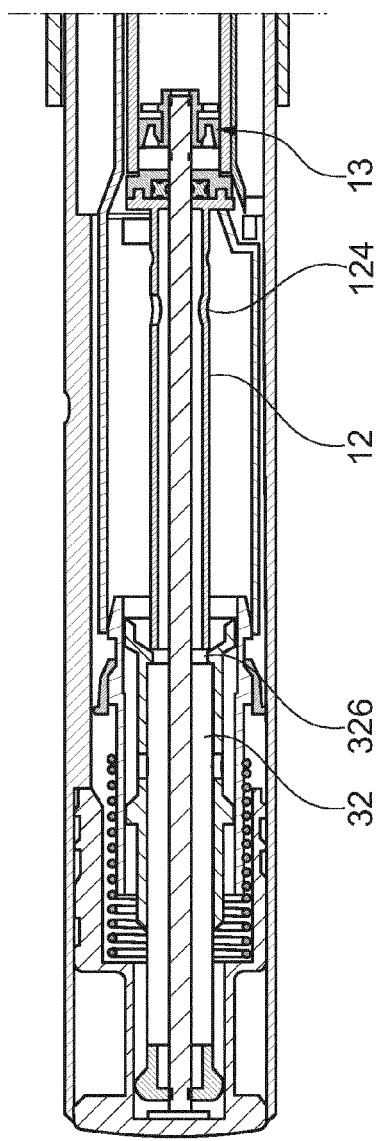
Fig. 18A
Fig. 18B

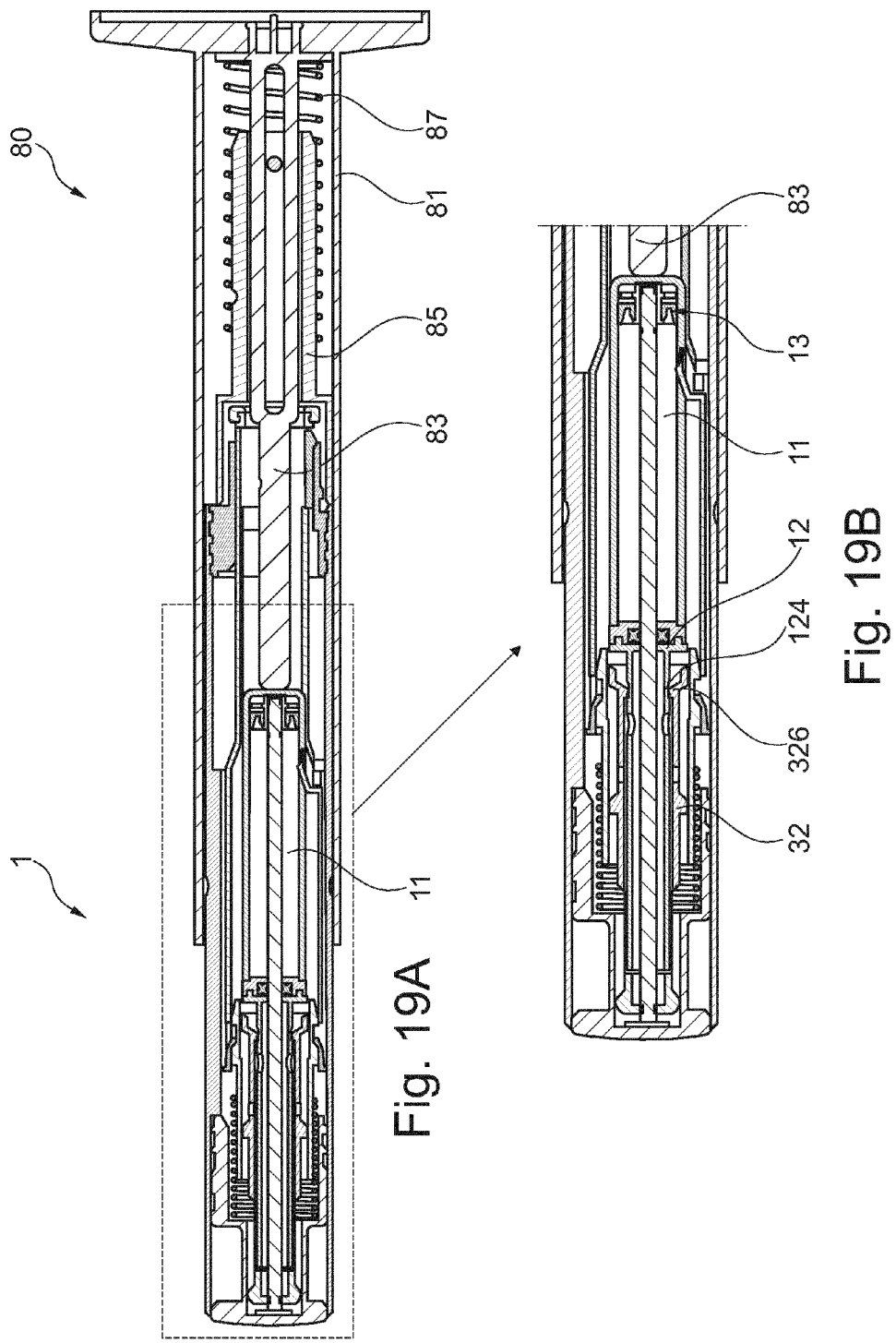

AUTOMATIC INJECTION TRAINING DEVICE

TECHNICAL FIELD

The present invention relates to automatic injection training devices, i.e. educational appliances or dummies to train individuals in the administration of medication by means of automatic injection devices. More specifically, the present invention relates to a training device that simulates the injection of a medicament by an automatic injection device more accurately by means of a damper unit and/or to a training device that has an actuation assembly that is configured such that the device can be reused easily. Further aspects of the invention relate to a reload unit for an automatic injection training device.

RELATED ART

Automatic injection devices for providing active substances (e.g., pen-type injectors) are well-known in the art. In many cases, training versions of such devices are required for showing potential users (e.g., patients or healthcare providers) how a device should be employed and for illustrating the advantages of the device. Such devices are frequently called "promotion" or "training" devices. The devices should mimic the function of a respective injection device but, preferably, should not inject an active substance (e.g., into a tissue of a patient or a user employing the device). More preferably, these promotion or training devices should not inject any substance at all.

U.S. Pat. No. 5,071,353 discloses a training device for an automatic injector. The device comprises a cylindrical outer sleeve in the rear portion of which a discharge mechanism is connected. The discharge mechanism comprises a plunger, a coil spring which acts on the plunger, a locking device, and a safety member. However, this device does not provide means allowing an accurate simulation of the resistance acting on the discharge mechanism of a regular injection device when an active substance is ejected.

WO 2011/151315 discloses a training cartridge for a drug delivery device as well as a method for resetting the cartridge. The cartridge comprises a body of substantially cylindrical shape, a piston that is slidably disposed in the body in an axial direction, and a closure means disposed at an axial end portion of the body. The piston and the closure means confine an interior volume coupled to the exterior via at least one fluid escape channel. According to the method disclosed, several steps are required for resetting the cartridge.

There remains a need for improved automatic injection training devices that can be reused more easily and/or more frequently. Also, reset appliances for such training devices are required.

Further, there remains a need for improved automatic injection training devices that provide a more accurate simulation of medicament injection.

SUMMARY OF THE INVENTION

In order to overcome one or several of the above-mentioned problems, an injection device according to claim 1 and an assembly according to claim 13 is provided.

Further aspects, improvements and variations are disclosed in the dependent claims, the figures and the description.

In the present application, when the term "distal" is used, this refers to the direction pointing away from the dose delivery site. When the term "distal part/end" is used, this refers to the part/end of the delivery device, or the parts/ends of the members thereof, which is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site. With the training device of the present invention, any suitable surface may form the dose delivery site (even if no dose is actually delivered).

Further, the term injection simulation preferably refers to the phase following actuation of the loaded device, i.e., the phase in which a regular automatic injection device would insert a needle into the patient's skin and/or inject an active substance. The training device of the present invention may be provided with a delivery member or an element resembling such delivery member but preferably does not comprise such delivery member (e.g., a needle).

The automatic injection training device of the present invention comprises a housing assembly, an actuation assembly, and a damper unit. The housing assembly has an outer housing. The damper unit has a damper housing and a piston assembly that is arranged in said damper housing. The damper housing and the piston assembly preferably are configured such that the damper housing slides in a proximal direction relative to the piston assembly during injection simulation.

The housing assembly of the device of the present invention may further comprise a proximal end cover and a distal end cover. The housing assembly may have an opening at its proximal end (e.g., an opening provided in the proximal end cover and extending along the longitudinal axis of the device). The opening may be covered by a removable cap.

The damper unit may be arranged in the outer housing. The damper housing may be slidably arranged in the outer housing and may be slidable along the longitudinal axis of the device. As such, the damper housing may slide in the proximal direction along the longitudinal axis of the device during injection simulation. The damper housing may be operationally associated with a first energy accumulating member such that, due to an output axial force from said first energy accumulating member, the damper housing is moveable in relation to the piston assembly and/or in relation to the outer housing towards the proximal end of the device from a loaded position to a position following injection simulation. The first energy accumulating member may be a first spring, for example a first helical spring.

The damper housing may contain a damper fluid that is sealed inside the damper. According to embodiments of the invention, the damper housing may have a cup-shaped structure that is sealed at the proximal end. Suitable damper fluids include gases and liquids, for example air or viscous fluids (e.g., grease).

The movement of the damper housing in the proximal direction preferably mimics the sound produced by regular injection devices at the start of penetration, providing users of the training device with a similar audible feedback. Additionally or alternatively, a sound element may be provided to produce an audible feedback when the damper housing reaches proximate the position following injection simulation. In embodiments, the damper housing may interact with said sound element, which may be a flexible lever connected to some other component of the device, for example a sleeve surrounding the damper housing.

The position of the piston assembly in relation to the outer housing may be substantially fixed during injection simulation. According to embodiments of the invention, the piston assembly may be coupled to a damper rod, which may be fixedly arranged at a distal end of the device. The damper rod may be held by an element of the housing assembly and/or an element of the actuation assembly, for example an actuator. The damper rod may act as a spring guide for the first helical spring.

The piston assembly may be configured to provide a first resistance to fluid flowing in a proximal direction therethrough and a second resistance to fluid flowing in a distal direction therethrough, the first resistance being greater than the second resistance. This, on one hand, may ensure that a realistic damping that mimics the injection of an active substance through a delivery member is provided during injection simulation when the device is activated. On the other hand, as will be explained in more detail below, the training device can be reloaded easily, requiring minimal force.

According to embodiments of the invention, the piston assembly may comprise a piston and a valve element. The piston may have one or several fluid passages and the valve element may be configured to obstruct or inhibit fluid flow through said passage/s in a certain direction. The piston may be arranged around a distal portion of the valve element and the fluid passage may be provided by a gap formed between the piston and the valve element. Alternatively or additionally, the distal portion of the valve element may be provided with recesses and/or cut-outs for providing one or several fluid passages in conjunction with the piston.

Preferably, the valve element obstructs or inhibits fluid from flowing through the passage in a proximal direction. The valve element may have a widened portion (e.g., a disc shaped structure) that provides one or several openings for fluid flowing therethrough and is located on a proximal side of the piston. The piston may be moveable in relation to the valve element. In particular, the piston may be configured to be moved in the proximal direction by fluid pressure when the damper housing is moved in the proximal direction. This may lead to an abutment surface of the piston being pressed against the valve element such that the opening/s of the valve element are sealed and flow through the passage is obstructed. Further, the piston may be configured to be moved in the distal direction by fluid pressure when the damper housing is moved in the distal direction, thereby separating the abutment surface from the opening/s and allowing fluid flow through said opening/s and through the fluid passage. The abutment surface may be a closed surface and may face in the proximal direction.

The piston may further comprise a tapered distal portion that tapers towards an inner wall of the damper housing in a distal direction.

The damper unit may further comprise a pusher element, which may have a proximal portion that is connected and/or fixed to the damper housing. According to embodiments of the invention, the pusher element may have a hollow distal portion that accommodates the damper rod and/or the first energy accumulating member. The output force from said first energy accumulating member may act upon the pusher element, which may transmit this force to the damper housing. The damper rod may extend into the damper housing through an opening in the proximal portion of the pusher element. The damper unit may further comprise a seal for ensuring that the damper fluid does not leak through the opening (e.g., when the damper housing is moved). The seal may interact with and/or seal against the damper rod.

Further, the seal may be arranged between the damper housing and the pusher element.

The pusher element may feature one or several recesses, projections and/or openings for being held by an element of the actuator assembly, for example the actuator. The recesses, projections and/or openings may be provided along a distal portion of the pusher element.

According to embodiments of the invention, the actuation assembly comprises a first sleeve, the actuator, and/or a second sleeve.

The first sleeve or actuator sleeve may be slidably arranged in relation to the outer housing and operationally associated with a second energy accumulating member such that, the first sleeve is axially moveable in relation to the outer housing towards the distal end of the device from a starting position to a retracted position against an axial force from said second energy accumulating member and/or such that, due to an output axial force from said second energy accumulating member, the sleeve is axially moveable in relation to the outer housing a predetermined distance towards the proximal end of the device from the retracted position to the starting position. The second energy accumulating member may be a second spring, for example a second helical spring. The second helical spring may be provided around the first sleeve and bear against the housing assembly (e.g., the distal end cover) and/or the actuator.

The sleeve may be formed as a hollow structure having a central opening configured for accommodating the actuator therein. In embodiments, an inner surface of the sleeve or ribs provided on such inner surface may taper towards the longitudinal axis of the device when following the sleeve in the distal direction.

The actuation assembly of devices according to the present invention may comprise the actuator, which may feature a biasable portion. The biasable portion may have a first segment that has a first outer diameter and a second segment that has a second outer diameter that is larger than the first outer diameter. According to embodiments of the invention, the second segment may be located proximal from the first segment. The biasable portion may be formed by resilient arms.

The position of the actuator along the longitudinal axis of the device may be substantially fixed in relation to the outer housing. When the damper housing is in the loaded position, the movement of the damper housing towards the proximal end of the device (e.g., to the position following injection simulation) may be substantially inhibited by the least one biasable portion interacting with the damper housing and/or the pusher element. The actuator may have the shape of a hollow body that has a central opening and accommodates the pusher element and/or the damper housing. The biasable portion may be provided with an inner protrusion that protrudes into a central opening of the actuator and engages the damper housing and/or the pusher element when the damper housing is in the loaded position. For example, the inner protrusion may engage openings, recesses and/or protrusions provided to the pusher element and/or the damper housing. The inner protrusion may be provided in the region of the second segment.

In the loaded position of the damper housing the biasable portion may be forced or biased in the outward direction due to the output axial force of the first energy accumulating member acting on the pusher element and/or the damper housing. However, when the first sleeve is in the starting position, it preferably overlaps at least part of the biasable portion and/or at least part of or the entire second segment, thereby obstructing or inhibiting the biasable portion from bending outwardly. The pusher element and/or the damper housing, hence, remain engaged by the biasable portion (e.g., its inner protrusion). The inner protrusion of the actuator and/or the opening, recess or protrusions of the pusher element may be tapered such that a force having an outward direction component acts on the biasable portion when the output axial force from the first energy accumulating member pushes the pusher element in the proximal direction.

The sleeve may further be arranged and/or configured such that the biasable portion bends outwardly and releases the damper housing and/or the pusher element from the loaded position when the first sleeve is moved in a distal direction (e.g., to the retracted position). For example, the first sleeve may be shaped such that an opening or a recess along an inner surface of the sleeve overlaps the biasable portion (in particular the second segment) when the sleeve is retracted. Alternatively or additionally, the proximal end of the first sleeve may be disposed distally from the biasable portion and/or distally of the second segment when the first sleeve reaches the retracted position.

The actuation assembly of devices according to the present invention may also comprise a second sleeve. This second sleeve may have the shape and function of a needle cover of regular automatic injection devices and, therefore, is also denominated "needle cover" in the context of the present invention.

The second sleeve may be operationally associated with the first sleeve and may have a proximal end that extends outwards of the housing assembly in a proximal direction when the sleeve is in the starting position. Preferably, the second sleeve is arranged such that it is slid in the distal direction in relation to the outer housing when a user presses the device onto a dose delivery site. In this context, the second sleeve may be slidably arranged in relation to the outer housing and moveable in relation to the outer housing towards the distal end of the device from a starting position to a retracted position against an axial force from an energy accumulating member, for example the second energy accumulating member. The second sleeve may protrude a first distance from the housing assembly when it is in the starting position and protrude a second distance from the housing assembly when it is in the retracted position, the second distance being smaller than the first distance. When the second sleeve is pressed against the dose delivery site, it preferably pushes the first sleeve in a distal direction (e.g., to its retracted position) such that the first sleeve frees and/or does not overlap the second segment of the biasable portion once the second sleeve reaches a predetermined position (e.g., the retracted position).

The second sleeve may also be arranged such that, due to an output axial force from an energy accumulating member (e.g., the second energy accumulating member), the second sleeve is axially moveable in relation to the outer housing a predetermined distance towards the proximal end of the device from the retracted position to the starting position. According to embodiments of the invention, the second sleeve is not locked in a proximal position (e.g., the starting position) after an injection simulation is performed.

The second sleeve may provide the sound element for producing a sound when the damper housing reaches proximate the position following injection simulation. For example, the needle cover may comprise a flexible lever that is actuated by the damper housing.

According to embodiments of the invention, a needle cover extension may be provided at the proximal end of the second sleeve. The needle cover extension may be fixed to the second sleeve and may interact with the proximal end cover to limit movement of the second sleeve in the distal direction. For example the needle cover extension may have a diameter that is larger than the diameter of the second sleeve and/or than the opening provided at the proximal end of the housing assembly (e.g., the opening provided in the proximal end cover).

The first sleeve and/or the actuator may be configured such that the second segment of the biasable portion is overlapped by the first sleeve again when the first sleeve is moved back to the starting position after the injection simulation is performed and the device is withdrawn from the dose delivery site. This may be facilitated by the actuator featuring a tapering segment between the first segment and the second segment and/or the sleeve featuring a tapered inner surface (see above).

According to embodiments of the invention the device may be configured for being reloadable. For this purpose, the damper housing may be axially moveable in relation to the outer housing and/or in relation to the piston assembly towards the distal end of the device from the position following injection simulation to the loaded position, preferably against the axial force from the first energy accumulating member. The biasable portion of the actuator may be configured to reengage the damper housing and/or the pusher element when the damper housing reaches the loaded position. As mentioned above, the biasable portion may be overlapped by the first sleeve and inhibited from bending outwards substantially (first sleeve in the starting position) when the device is withdrawn from the delivery site. Preferably, the biasable portion can still be extended slightly, such that the pusher element can be slid along the inner protrusion of the actuator until said inner protrusion engages the opening, recess and/or protrusion of the pusher element again.

As will be apparent to those skilled in the art from the instant description, an inner opening or recess may be provided to the biasable portion instead of or additionally to the inner protrusion described above when a corresponding outer protrusion is provided to the pusher element and/or the damper housing.

In order to facilitate reloading of training devices, the present invention further relates to a reload unit. The reload unit may be provided in an assembly comprising said reload unit and any of the devices described above.

The reload unit may comprise a shaft member, an ejector and/or a stand. The stand that may have a first portion that may be configured for accommodating the housing assembly of the training device therein. The first portion may be a hollow and substantially cylindrical structure that extends along the longitudinal axis of the device when the reload unit is arranged for a reload procedure. Additionally or alternatively, the stand may have a second portion configured to provide a base for supporting the reload unit in an upright position.

The shaft member may be arranged inside the first portion of the stand. The shaft member may be configured to extend through a proximal opening of the needle cover such that the damper housing can be pushed in the distal direction by means of the shaft. The length of the shaft member may be sufficient for pushing the damper housing from the position following injection simulation to the loaded position. Preferably, the shaft member is a separate element that is fixed to the second portion of the stand. In order to reload the device, it may be introduced into the stand and pressed towards the base. The device, hence, is moved in the axial direction in relation the fixed shaft member, which will extend into the device and push the damper housing in the distal direction.

The ejector may be configured for ejecting the housing from the reload unit after the reload procedure is completed. For this purpose, the ejector may be slidably arranged in relation to the shaft member and operationally associated with a third energy accumulating member such that the ejector is axially moveable in relation to the shaft member from a starting position to a retracted position against an axial force from said third energy accumulating member and/or such that, due to an output axial force from said third energy accumulating member, the ejector is axially moveable in relation to the shaft member from the retracted position to the starting position. The third energy accumulating member may be a third spring, for example a third helical spring.

In order to prevent activation of the device during the reload procedure, the ejector may have a first end with a cup-shaped structure that is configured to accommodate the proximal end of the needle cover extending out of the housing assembly and to bear against an abutment surface of said housing assembly when the device is being reloaded. The cup-shaped structure, therefore, avoids that the needle cover is moved in the distal direction, which could lead to activation of the actuation assembly. The ejector may be operationally coupled with the shaft member such that the ejector is inhibited from falling out of the stand. For example, the ejector may be provided with a pin that extends through an opening of the shaft member.

Aspects of the invention may relate to the reload unit or the damper unit described above as stand-alone components.

BRIEF DESCRIPTION OF THE DRAWINGS

The following Figures below disclose an embodiment of the invention for illustrational purposes only. In particular, the disclosure within the Figures is not meant to limit the range of protection of the invention. The embodiment shown may be modified in many ways within the scope of the claims.

FIG. 1: Perspective view of a device according to an embodiment of the present invention.

FIG. 2: Exploded view of a housing assembly of the device of FIG. 1.

FIG. 7: Exploded view of an actuation assembly of the device of FIG. 1.

FIG. 8A: Perspective view of an actuator of the actuation assembly of FIG. 7.

FIG. 8B: Top view of the actuator of FIG. 8A.

FIG. 8C: Sectional view of the actuator of FIG. 8A.

FIG. 9A: Perspective view of a first sleeve of the actuation assembly of FIG. 7.

FIG. 9B: Sectional view of the first sleeve of FIG. 9A.

FIG. 10A: Perspective view of a needle cover of the actuation assembly of FIG. 7.

FIG. 10B: Sectional view of the needle cover of FIG. 10A.

FIG. 11-16: Sectional views of the delivery device of FIG. 1 illustrating preparation, activation, injection simulation and dose delivery site withdrawal.

FIG. 17A: Exploded view of a reload unit according to embodiments of the present invention.

FIG. 17B: Sectional view of the reload unit of FIG. 17A in an assembled state.

FIG. 18A: Sectional view of a device according to the present invention in a position following injection simulation with the reload unit of FIG. 17A arranged at the proximal end.

FIG. 18B: Enlarged view of the distal part of the device shown in FIG. 18A, illustrating details of the actuation assembly.

FIG. 19A: Sectional view of the device and the reload unit of FIGS. 18A and 18B with the damper housing in the loaded position following reloading.

FIG. 19B: Enlarged view of the distal part of the device shown in FIG. 19A, illustrating details of the actuation assembly.

DETAILED DESCRIPTION OF THE DRAWINGS

Figure 3:
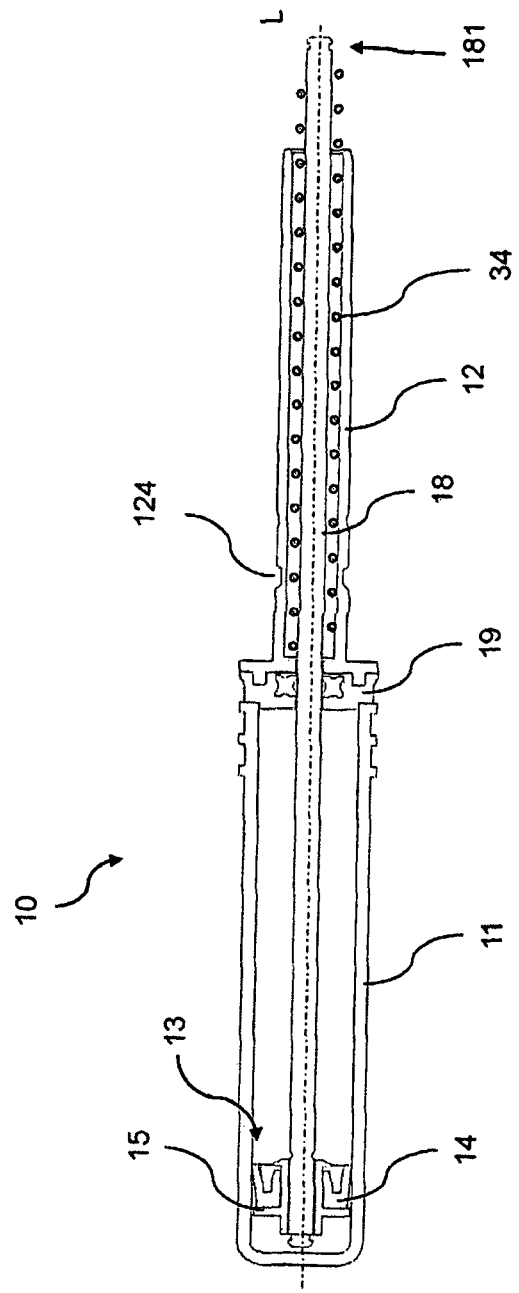
FIG. 3: Sectional view of a damper unit of the device of FIG. 1.

As shown in FIG. 1, a device 1 according to the present invention may comprise a housing assembly 2 and extend along a longitudinal axis L. The housing assembly 2 may be open at the proximal end (not shown) and can be closed with a removable cap 9. As further illustrated in FIG. 2, the housing assembly 2 may comprise an outer housing 3, a proximal end cover 4 with an opening 5 extending along the longitudinal axis L, and a distal end cover 6. The proximal end cover 4 may be inserted into the outer housing 3 and fixed therein such that the opening 5 is coaxial with the longitudinal axis L. The outer housing 3 may comprise an inspection window (not shown) for assessing the position of the damper housing and/or the state of the actuation assembly.

Figure 4:
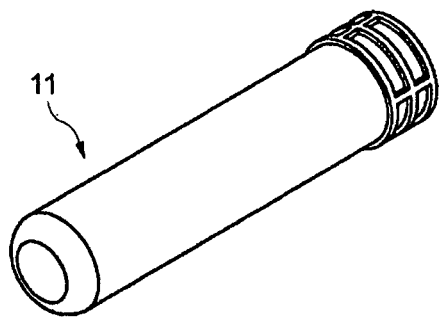
FIG. 4: Perspective view of a damper housing of the damper unit of FIG. 3.

FIG. 3 shows a sectional view along the longitudinal axis L of a damper unit 10 that may be inserted into the outer housing 3 of the device 1 of FIG. 1. The damper unit 10 comprises a damper housing 11 and a piston assembly 13 with a piston 14 and a valve element 15 that is arranged in said damper housing 11. The damper unit 10 illustrated in FIG. 3 further features a pusher element 12, a damper rod 18, and a seal 19. The pusher element 12 is fixedly attached to the damper housing 11, the seal 19 being arranged and held between these two components. As can also be seen in FIG. 4, the damper housing 11 has a cup-shaped structure that is closed at the proximal end. The damper fluid (e.g., air or grease), hence, is sealed in the damper housing 11. No fluid passage through which the damper fluid might escape is provided in the proximal part and/or the distal part of the damper housing 11.

As further shown in FIG. 3, the piston assembly 13, more specifically the valve element 15, may be fixed to the damper rod 18, which extends into the damper housing 11 and through the pusher element 12 from a distal fixation point 181. The piston assembly 13, therefore, is substantially fixed in relation to the housing assembly.

Meanwhile, the damper housing 11 may be slidably arranged in the outer housing of the device 1 along the longitudinal axis L and may be slid in the proximal direction along the longitudinal axis L of the device during injection simulation. For this purpose, the pusher element 12 is associated with a first energy accumulating member in the form of a first helical spring 34 that is arranged around the damper rod 18. As will be explained below, when an injection is simulated, the pusher element 12 and the damper housing 11 are moved in relation to the piston assembly 13 towards the proximal end of the device 1 by the output axial force from said first helical spring 34, thereby pressing the damper fluid in a proximal direction through the piston assembly 13.

In order to provide a realistic damping effect that simulates the damping occurring when an active substance is delivered through a delivery member (e.g. a needle or nozzle of a regular automatic injection device) but still allow easy reset, the piston assembly 13 of the present invention may be configured to provide a first resistance to fluid flowing in a proximal direction therethrough and a second resistance to fluid flowing in a distal direction therethrough, wherein the first resistance is greater than the second resistance.

Figure 5A:
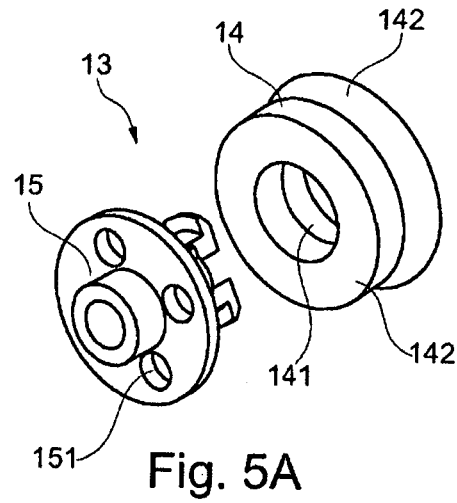
FIG. 5A: Perspective view of a piston assembly of the damper unit of FIG. 3.
Figure 5B:
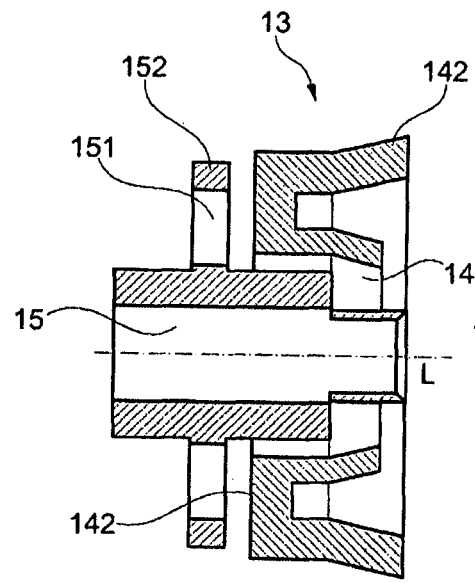
FIG. 5B: Rotated sectional view showing the piston assembly of FIG. 5A in the open position.

As most clearly shown in FIG. 5B, which depicts another sectional view of the piston assembly 13 that is rotated for 90° with respect to the view of FIG. 3, a fluid passage 141 extends through the piston assembly 13. In the shown embodiment, the fluid passage 141 is provided between a central opening of the piston 14 and the distal portion of the valve element 15, which has a smaller outer diameter than the inner diameter of the central opening. Furthermore, the valve element 15 is provided with cut-outs.

Figure 5C:
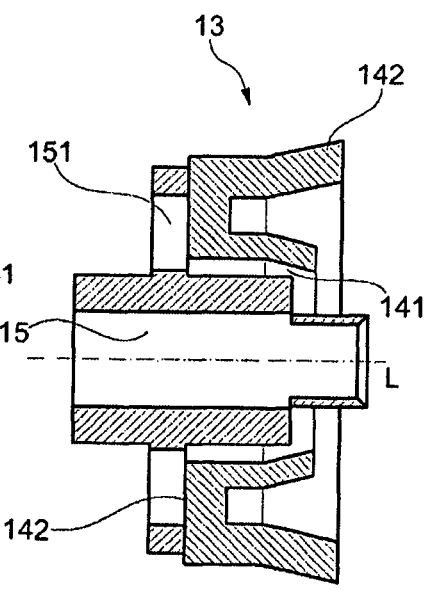
FIG. 5C: Rotated sectional view showing the piston assembly of FIG. 5A in the closed position.

When fluid pressure on the proximal side of the piston assembly 14 is higher than on the distal side (damper housing 11 being moved in the distal direction when the device is being reloaded), the piston assembly 14 assumes the position of FIG. 5B, where the damper fluid can easily flow through openings 151 in a widened portion 152 of the valve element 15 and through the fluid passage 141 (see also FIG. 5A). In contrast, when fluid pressure on the distal side of the piston assembly 14 is higher than on the proximal side (damper housing 11 being moved in the proximal direction during injection simulation), the piston 14 is moved towards the valve element 15 such that the abutment surface 142 obstructs fluid flow through the openings 151. As shown in FIG. 5C, the opening 151 is covered almost completely, such that fluid flow is restricted substantially.

Figure 6A:
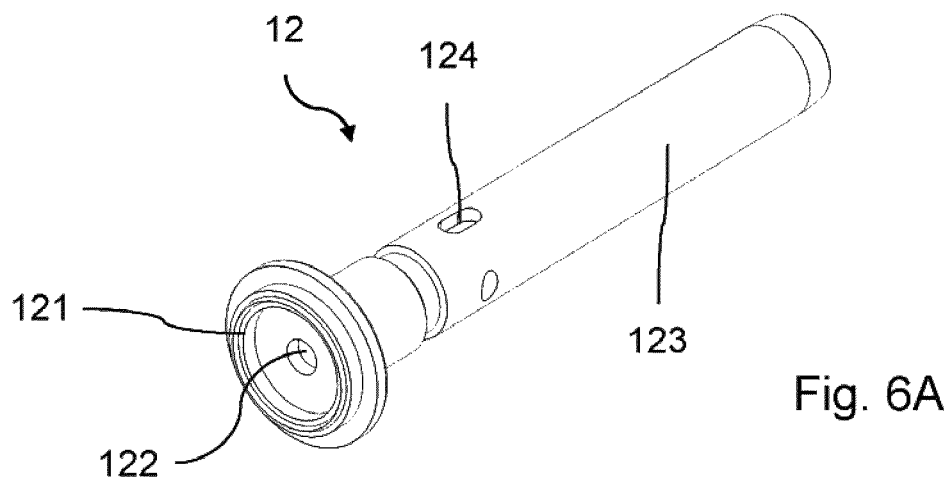
FIG. 6A: Perspective view of a pusher element of the damper unit of FIG. 3.
Figure 6B:
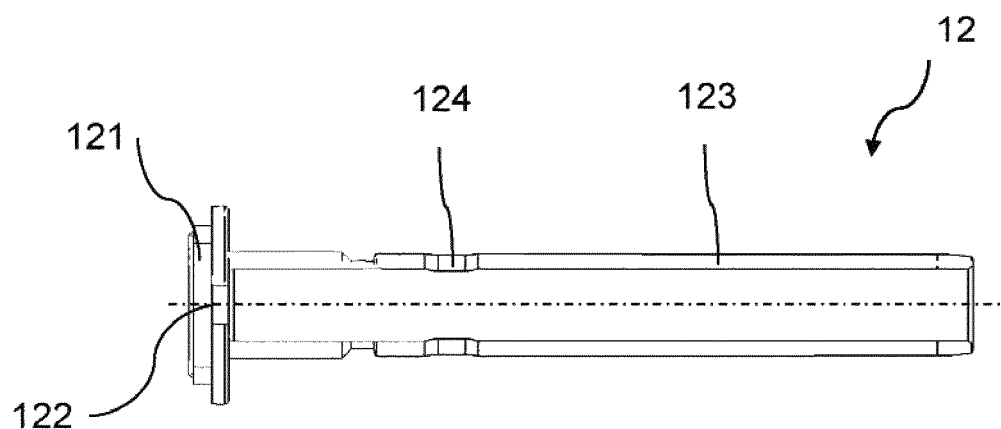
FIG. 6B: Sectional view of the pusher element of FIG. 6A.

FIGS. 6A and 6B show perspective and sectional views of the pusher element 12 of FIG. 3, respectively. As shown therein, the pusher element 12 may have a proximal portion 121 that may be configured for attachment to the damper housing 11 and/or the seal 19. The distal portion 123 of the pusher element 12 may be hollow and may be configured to accommodate the damper rod 18 therein, which may extend into the damper housing 11 through a hole 122 in the proximal portion 121.

In order to hold the damper housing and the pusher element in the loaded position, the pusher element 12 has openings 124, into which a protrusion of the actuator may extend, as will be described below in more detail. Recesses or protrusions (not shown) may be provided instead of or in addition to the openings 124.

FIG. 7 shows an exploded view of an actuation assembly 30 that may be used for a device 1 according to the present invention. The actuation assembly 30 comprises a first sleeve 33 that is operationally associated with a second energy accumulating member in the form of a second helical spring 35, an actuator 32, and a needle cover 31. A needle cover extension 39 may be provided at the proximal end of the needle cover 31.

As illustrated in FIGS. 8A-8C, the actuator 32 may be a generally tubular structure with a central opening 327 that extends along the longitudinal axis L of the device. The central opening 327 may be configured for accommodating the pusher element and/or the damper rod. A distal portion 328 may provide one or more attachment structures 329 for engaging the actuator 32 with the outer housing and/or the distal end cover. A further attachment structure may also engage the damper rod 18 and hold it in a fixed manner.

The actuator 32 may have a biasable portion 322, which is formed by resilient arms in the illustrated embodiment. The biasable portion 322 has an inner protrusion 326 that extends into the central opening 327 and preferably is formed proximate the proximal end of the biasable portion 322. Further, the biasable portion 322 has a first segment 323 with a first outer diameter and a second segment 324 with a second outer diameter that is larger than said first outer diameter. A tapering segment 325 extending between said first and second segments 323, 324 that preferably tapers away from the longitudinal axis L of the device 1 in the proximal direction may also be provided. As shown also in FIGS. 8B and 8C, the second segment 324 may be more proximal than the first segment 323 when the actuator 32 is assembled in the device 1. The inner protrusion 326 may be provided in the region of the second segment 324. In other embodiments, an opening or recess may be provided instead of the inner protrusion 326.

FIGS. 9A and 9B show perspective and sectional views of the first sleeve 33. The sleeve 33 is formed by a tubular structure with a central opening 337. The central opening 337 may extend along the longitudinal axis L of the device and may be configured for accommodating the actuator 32.

The first sleeve 33 is pushed in a proximal direction to its starting position by the output axial force of the second helical spring 35 that is operationally associated with said first sleeve 33 and bears, for example, against the distal end cover 6. When the first sleeve 33 is in said starting position, it covers the biasable portion 322 of the actuator 32. The biasable portion 322, therefore, is substantially inhibited from bending outward. With the inner protrusion 326 of the actuator 32 engaging the opening 124 of the pusher element 12, the pusher element 12 is secured in the loaded position and inhibited from moving in the proximal direction in relation to the outer housing 3 and the piston assembly 13. As will be described below, the first sleeve 33 is pushed in the distal direction when the device is pressed against a dose delivery site, freeing the biasable portion 322 and, thereby, the pusher element 12.

Along the inner surface of the central opening 337, between a proximal end 331 and a distal end 335 of the first sleeve 33, ribs 333 may be provided. The ribs 333 preferably abut against the actuator 32, for example against the tapering segment 325 of the actuator 32, when the sleeve 33 reaches its starting position and inhibit the sleeve 33 from moving further in the proximal direction due to the output axial force of the second helical spring 35 that is operationally associated with said sleeve 33 (see also FIG. 7).

FIGS. 10A and 10B show perspective and sectional views of the needle cover 31, respectively. As shown in these Figures, also the needle cover 31 may be formed as a generally tubular structure with a central opening extending therethrough and providing an opening at a proximal end 311. One or several cut-outs 313 may be arranged in the needle cover 31 such that the position of the damper housing 11 can be assessed by looking through the inspection window provided in the outer housing 3, when the needle cover 31 is placed in the housing assembly 2. A distal end 314 of the needle cover 31 may abut a protrusion or collar 334 of the first sleeve 33 such that the needle cover 31 is forced in the proximal direction together with the first sleeve 33 by the output axial force of the second helical spring 35.

FIG. 11 illustrates a training device 1 according to embodiments of the present invention in an initial, loaded position with the cap 9 covering the proximal end of the device 1. In FIG. 12 the cap 9 is removed, such that the device 1 is prepared for being used. As can be seen in these Figures, the first sleeve 33 and the needle cover 31 are forced in the proximal direction by the second helical spring 35. The first sleeve 33 and the needle cover 31 are in the starting position.

The proximal end 311 of the needle cover 31 extends out of the housing assembly 2 a first distance through an opening provided in the proximal end cover 4.

With the first sleeve 33 in the starting position, the sleeve 33 covers the biasable portion 322 of the actuator 32, also overlapping the second segment 324. The biasable portion, therefore, is inhibited from bending outward in a substantial manner. As a result, the pusher element 12 is secured in the loaded position by the inner protrusion 326 of the actuator 32 engaging the opening 124 of the pusher element 12. The damper housing 11 and the pusher element 12, hence, are inhibited from moving in the proximal direction in relation to the outer housing 3 and the piston assembly 13.

When the device 1 is pressed against a surface serving as a dose delivery site during the training procedure, the needle cover 31 and the first sleeve 33 are moved in the distal direction in relation to the outer housing 3 from the starting position (see FIG. 12) to a retracted position (see FIG. 13) in which the proximal end 311 of the needle cover 31 extends out of the housing assembly 2 a second distance that is smaller than the first distance of the starting position. In alternative embodiments, the needle cover 31 may be pushed into the housing assembly 2 completely.

In the retracted position, the first sleeve 33 frees the second segment 324 of the biasable portion 322. For example, as shown in the illustrative embodiment of FIG. 13, the proximal end of the first sleeve 33 does not overlap the entire biasable portion anymore when the sleeve 33 is moved to the retracted position. The biasable portion 322 (i.e., the resilient arms of the actuator 32), therefore, will be bend outwardly by an output axial force from the first helical spring 34 that acts on the pusher element 12 and is transmitted to the biasable portion 322 along the inner protrusion 326. In consequence, the pusher element 12 and the damper housing 11 will be released by the inner protrusion 326 and move in the proximal direction to a position following injection simulation due to said output axial force from the first helical spring 34 (see FIG. 14). The movement of the damper housing 11 in the proximal direction is retarded by the piston 13 in order to provide a realistic simulation of medicament delivery. When moving in the proximal direction, the damper unit may also mimic the sound produced by regular injection devices at the start of penetration and provide users of the training device 1 with a similar audible feedback. The sound may be produced, for example, by the damper fluid flowing through the piston assembly 13 and/or sliding of the piston assembly 13 along the damper housing 11.

FIG. 15, which illustrates a sectional view of the device 1 in the position of FIG. 14 when rotated by 90°, shows that the needle cover 31 may be provided with a lever 315. The lever 315 interacts with the damper housing 11 such that an additional audible feedback is emitted when the damper housing 11 reaches proximate the position following injection simulation. Feedback mechanism may also be provided to other components of the device 1, additionally or alternatively to the lever 315.

When the device 1 is withdrawn from the surface serving as the dose delivery site (FIG. 16), the first sleeve 33 and the needle cover 31 are moved from the retracted position to the starting position due to the output axial force of the second helical spring 35. In the illustrative embodiment, the needle cover remains unlocked afterwards.

FIGS. 17A and 17B illustrate a reload unit 80 according to the present invention in an exploded and in an assembled state, respectively. As shown, the reload unit 80 may have a stand 81 with a hollow first portion 812 that is shaped to accommodate therein the outer housing of delivery devices according to the present invention. Further, a base 814 may be provided.

A shaft member 83 with a shaft 831 is arranged in the first portion 812 and fixed to the base 814. The longitudinal axis of the shaft 831 and the longitudinal axis of the first portion 812 of the stand preferably are congruent. As also shown in FIG. 18A, the shaft 831 may be configured such that it can be inserted into the device 1 through the central opening of the needle cover 31. The device 1 may be reloaded by introducing the shaft 831 through said central opening and pushing the damper housing 11 in the distal direction from the position following injection simulation (FIGS. 18A and 18B) to the loaded position (FIGS. 19A and 19B). The damper housing 11 and the pusher element 12 will be moved in the distal direction against the axial force of the first helical spring (not shown) until the inner protrusion 326 engages the opening 124 and secures the pusher element 12 in the loaded position. The movement can be performed easily since the piston assembly 13 provides a relatively low resistance to fluid flowing in the distal direction therethrough. With the first sleeve 33 in the starting position (see FIGS. 11 and 12), the damper housing 11 remains in the loaded position until the actuation assembly is activated again.

Once reloading of the device 1 is completed, the device 1 may be ejected from the reload unit 80 by means of an ejector 85. The ejector 85 is moved from a starting position (FIG. 18A) to a retracted position (FIG. 19A) against the output axial force of a third energy accumulating member in the form of a third helical spring 87 when the device is being reloaded. Therefore, the third helical spring 87 will force the ejector back into its starting position when the force exerted during the reload procedure (e.g., by a user reloading the device 1) is released and eject the device 1 from the reload unit 80. In the illustrated embodiment, the ejector 85 has a cup-shaped structure 852 at a first end, which is the end of the ejector 85 that interacts with the device 1. The cup-shaped structure is shaped to accommodate the proximal end 311 of the needle cover 31 extending out of the housing assembly so that the actuation assembly is not activated during the reload procedure.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above.

Furthermore, in the claims the word "comprising" does not exclude other elements or steps, and the indefinite article "a" or "an" does not exclude a plurality. A single unit may fulfill the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. An automatic injection training device, comprising:
a housing assembly, including an outer housing; and
a damper unit, including a damper housing and a piston assembly arranged in the damper housing, wherein the damper housing slides in a proximal direction relative to the piston assembly when an injection is simulated; and the piston assembly comprises a piston, a valve element, and a fluid passage; and the piston cooperates with the valve element to obstruct flow of fluid through the passage in the proximal direction; and
an actuation assembly that comprises a sleeve that is slidably arranged in relation to the outer housing and operationally associated with a second energy accumulating member such that the sleeve is axially movable in relation to the outer housing toward a distal end of the device from a starting position to a retracted position against an axial force from the second energy accumulating member or such that due to the axial force from the second energy accumulating member, the sleeve is axially movable in relation to the outer housing a predetermined distance toward a proximal end of the device from the retracted position to the starting position;
wherein the damper housing is operationally associated with a first energy accumulating member such that, due to an axial force from the first energy accumulating member, the damper housing moves in relation to at least one of the piston assembly and the outer housing toward a proximal end of the automatic injection training device from a loaded position to a position following a simulated injection.

2. The device of claim 1, wherein a position of the piston assembly in relation to the outer housing is substantially fixed during a simulated injection.

3. The device of claim 1, wherein the piston assembly is configured to provide a first resistance to fluid flowing in a proximal direction therethrough and a second resistance to fluid flowing in a distal direction therethrough, the second resistance being smaller than the first resistance.

4. The device of claim 1, wherein the actuation assembly comprises an actuator that has a biasable portion with a first segment having a first outer diameter and a second segment having a second outer diameter, the second segment being more proximal than the first segment and the second outer diameter being larger than the first outer diameter; and the sleeve overlaps at least part of the second segment and inhibits the biasable portion from moving in an outward direction when the sleeve is in the starting position.

5. The device of claim 4, wherein the actuator further has a tapering segment between the first segment and the second segment.

6. The device of claim 4, wherein when the damper housing is in the loaded position, movement of the damper housing toward the proximal end of the device is substantially inhibited by interaction of the least one biasable portion with at least one of the damper housing and a pusher element connected with the damper housing.

7. The device of claim 6, wherein when the damper housing is in the loaded position and the sleeve is moved to the retracted position, the biasable portion bends outwardly and releases the damper housing and/or the pusher element.

8. The device of claim 1, wherein the damper housing is axially movable in relation to at least one of the outer housing and the piston assembly toward a distal end of the device from the position following the simulated injection to the loaded position against the axial force from the first energy accumulating member.

9. The device of claim 1, wherein the actuation assembly further comprises a needle cover that is operationally associated or formed integrally with the sleeve and has a proximal end that extends outward of the housing assembly in the proximal direction when the sleeve is in the starting position.

10. An assembly, comprising:
the automatic injection training device of claim 1, and
a reload unit, comprising a shaft member configured for introduction into the outer housing through a proximal opening of a needle cover.

11. The assembly of claim 10, further comprising an ejector slidably arranged in relation to the shaft member and operationally associated with a third energy accumulating member such that the ejector is axially movable in relation to the shaft member from a starting position to a retracted position against an axial force from the third energy accumulating member and from the retracted position to the starting position, wherein the ejector has a first end with a cup-shaped structure configured to accommodate a proximal end of the needle cover extending out of the housing assembly therein and to bear against an abutment surface of the housing assembly when the automatic injection training device is being reloaded.

12. The assembly of claim 10, further comprising an ejector slidably arranged in relation to the shaft member and operationally associated with a third energy accumulating member such that the ejector is axially movable in relation to the shaft member from a starting position to a retracted position against an axial force from the third energy accumulating member and from the retracted position to the starting position, wherein the reload unit further comprises a stand having at least one of a first portion configured to accommodate and/or guide the housing assembly and a second portion configured to support the reload unit in an upright position.

13. The assembly of claim 12, wherein the ejector has a first end with a cup-shaped structure configured to accommodate a proximal end of the needle cover extending out of the housing assembly therein and to bear against an abutment surface of the housing assembly when the automatic injection training device is being reloaded.

* * * * *